US010524647B2

(12) United States Patent
Yu et al.

(10) Patent No.: US 10,524,647 B2
(45) Date of Patent: Jan. 7, 2020

(54) SMARTPHONE ENDOSCOPE SYSTEM

(71) Applicants: Bing Yu, Hudson, OH (US); Vivek Krishna Nagarajan, Akron, OH (US)

(72) Inventors: Bing Yu, Hudson, OH (US); Vivek Krishna Nagarajan, Akron, OH (US)

(73) Assignee: The University of Akron, Akron, OH (US)

( * ) Notice: Subject to any disclaimer, the term of this patent is extended or adjusted under 35 U.S.C. 154(b) by 412 days.

(21) Appl. No.: 15/500,626

(22) PCT Filed: Jul. 31, 2015

(86) PCT No.: PCT/US2015/043100
§ 371 (c)(1),
(2) Date: Jan. 31, 2017

(87) PCT Pub. No.: WO2016/019235
PCT Pub. Date: Feb. 4, 2016

(65) Prior Publication Data
US 2017/0209033 A1    Jul. 27, 2017

Related U.S. Application Data

(60) Provisional application No. 62/031,415, filed on Jul. 31, 2014, provisional application No. 62/078,002, filed on Nov. 11, 2014.

(51) Int. Cl.
*A61B 1/07* (2006.01)
*A61B 1/04* (2006.01)
(Continued)

(52) U.S. Cl.
CPC .................. *A61B 1/07* (2013.01); *A61B 1/00* (2013.01); *A61B 1/00105* (2013.01);
(Continued)

(58) Field of Classification Search
CPC ... A61B 1/00105; A61B 1/00167; A61B 1/04; A61B 1/042; A61B 1/043; A61B 1/053;
(Continued)

(56) References Cited

U.S. PATENT DOCUMENTS 6,524,237 B1 *   2/2003  McGowan ............... G02B 6/04
                                                348/E7.087
6,571,118 B1 *   5/2003  Utzinger ............. A61B 5/0071
                                                      356/318
(Continued)

FOREIGN PATENT DOCUMENTS

WO          9115793 A1    10/1991

*Primary Examiner* — John P Leubecker
(74) *Attorney, Agent, or Firm* — Renner Kenner Greive Bobak Taylor & Weber (57) ABSTRACT

A smartphone endoscope system includes a smartphone with first and second imaging sensors, and an imaging optics attachment. The imaging optics attachment includes a first and second imaging apparatus, the first imaging apparatus including a first light source, a beam splitter, an objective lens, and a fiber optic imaging bundle, wherein the fiber optic imaging bundle delivers excitation light to a target which emits a fluorescence emission and a reflectance emission both collected by the fiber optic imaging bundle and transmitted to the first imaging sensor. The second imaging apparatus includes a second light source, a DRS source fiber delivering broadband light to the target which produces a diffuse reflectance emission, a DRS detection fiber, a collimator, a slit, and a transmission grating wherein the transmission grating diffracts diffuse reflectance emission and creates diffracted light which is transmitted to a second imaging sensor.

13 Claims, 3 Drawing Sheets

(51) Int. Cl.
*G01J 3/36* (2006.01)
*G01J 3/44* (2006.01)
*A61B 5/00* (2006.01)
*A61B 1/00* (2006.01)
*A61B 1/06* (2006.01)
*G01J 3/02* (2006.01)

(52) U.S. Cl.
CPC ............ *A61B 1/00167* (2013.01); *A61B 1/04* (2013.01); *A61B 1/043* (2013.01); *A61B 1/0638* (2013.01); *A61B 1/0684* (2013.01); *G01J 3/0218* (2013.01); *G01J 3/0291* (2013.01); *G01J 3/36* (2013.01); *G01J 3/4406* (2013.01); *A61B 5/0071* (2013.01); *A61B 5/6898* (2013.01)

(58) Field of Classification Search
CPC ....... A61B 1/0638; A61B 1/0684; A61B 1/07; A61B 5/6898; A61B 5/0071; A61B 5/0075; A61B 5/0084; A61B 5/0086; H04N 5/2254; H04N 5/2256; H04N 2005/2255; G01J 3/0218; G01J 3/0205; G01J 3/0291; G01J 3/18
See application file for complete search history.

(56) References Cited

U.S. PATENT DOCUMENTS

| | | | | |
|---|---|---|---|---|
| 6,922,583 | B1* | 7/2005 | Perelman | A61B 5/0075 600/476 |
| 9,733,460 | B2* | 8/2017 | Kang | G02B 21/0064 |
| 2004/0037554 | A1* | 2/2004 | Ferguson | G02B 6/04 398/28 |
| 2006/0215013 | A1* | 9/2006 | Jongsma | A61B 1/00016 348/14.08 |
| 2007/0173718 | A1* | 7/2007 | Richards-Kortum | A61B 1/00096 600/431 |
| 2008/0137363 | A1* | 6/2008 | Harris | A61B 1/00096 362/574 |
| 2008/0207996 | A1* | 8/2008 | Tsai | A61B 1/00048 600/112 |
| 2010/0020320 | A1* | 1/2010 | Yao | G01J 3/2803 356/319 |
| 2010/0128221 | A1 | 5/2010 | Muller et al. | |
| 2010/0234684 | A1* | 9/2010 | Blume | A61B 1/00165 600/104 |
| 2011/0059016 | A1* | 3/2011 | Ramanujam | A61B 5/0059 424/9.1 |
| 2011/0137126 | A1* | 6/2011 | French | A61B 1/00165 600/178 |
| 2011/0295541 | A1* | 12/2011 | Yu | G01J 3/02 702/104 |
| 2012/0075619 | A1 | 3/2012 | Nieman et al. | |
| 2012/0281218 | A1* | 11/2012 | Schnitzer | A61B 1/043 356/432 |
| 2012/0283516 | A1* | 11/2012 | Kang | A61B 1/0623 600/182 |
| 2013/0128223 | A1 | 5/2013 | Wood et al. | |
| 2013/0137944 | A1* | 5/2013 | Jeong | A61B 1/015 600/317 |
| 2013/0300919 | A1* | 11/2013 | Fletcher | H04M 1/21 348/360 |
| 2014/0051923 | A1* | 2/2014 | Mirza | A61B 1/00126 600/103 |
| 2014/0142390 | A1 | 5/2014 | Bromwich | |
| 2014/0276111 | A1* | 9/2014 | Gal | A61B 1/00167 600/478 |
| 2015/0055137 | A1* | 2/2015 | Brown | G01B 9/02091 356/479 |
| 2016/0045102 | A1* | 2/2016 | Yu | A61B 1/07 600/427 |
| 2016/0296112 | A1* | 10/2016 | Fletcher | A61B 3/14 |
| 2016/0334610 | A1* | 11/2016 | Kang | G02B 21/0064 |
| 2017/0236281 | A1* | 8/2017 | Dacosta | G06T 7/0016 382/128 |

* cited by examiner

SMARTPHONE ENDOSCOPE SYSTEM

CROSS-REFERENCE TO RELATED APPLICATIONS

The present application claims priority to U.S. Provisional Patent Application Ser. No. 62/031,415, filed Jul. 31, 2014, and U.S. Provisional Patent Application Ser. No. 62/078,002, filed Nov. 11, 2014, the entireties of which are incorporated herein by reference.

FIELD OF THE INVENTION

The present invention generally relates to a smartphone endoscope system for medical imaging.

BACKGROUND OF THE INVENTION

Optical endoscopy is a powerful tool for noninvasive imaging within hollow tissue cavities through a catheter or minimally invasive imaging deep within tissue through a needle or laparoscopic/robotic instrument. In the past decade, various imaging modalities, including confocal microscopy, narrow-band imaging (NBI), fluorescence imaging (FLI), Raman imaging, optical coherent tomography (OCT), and photoacoustic imaging (PAI), with cellular to subcellular resolution have been successfully incorporated into endoscopes. These high resolution endoscopes have significantly improved the accuracy for disease diagnosis (such as early cancer detection) and treatment efficacy. In particular, endoscopic NBI employs blue or green light at peak absorption wavelengths of hemoglobin and can be used to enhance visualization of the mucosal surface structure and vascular network that cannot be observed using white light endoscopy. Endoscopic FLI with a fluorescence dye (e.g., proflavine) allows imaging of subcellular organelles, such as cell nuclei of epithelial tissue. Recent years have also seen increasing research on the integration of multiple imaging modalities into a single high-resolution fiber optic endoscope to obtain complementary tissue information. Most optical endoscopes employ an optical fiber, fiber optic imaging bundle, or light-guide for light delivery and collection.

Additionally, diffuse reflectacnce spectroscopy (DRS) with a fiber optic probe can noninvasively quantify the optical properties of epithelial tissues and has shown the potential as a cost-effective, fast and sensitive tool for diagnosis of early precancerous changes in multiple organ sites, including colon, cervix, oral cavity, breast, and gastrointestinal (GI) tracts. The major drawbacks of these high-resolution endoscopes are the use of expensive (over $10,000), bulky and power-consuming optical components (e.g., thermal lamps, cooled CCD cameras, discrete lens and filters, spectrographs, and power supplies). They often need experienced engineers to operate the sophisticated instruments and physicians to interpret the images, making them unaffordable to LMIC. In addition, many systems require a scanning mirror inside the endoscopes, which is bulky and incompatible with magnetic resonance imaging (MRI) and computer tomography (CT) scanners.

Meanwhile, billions of people worldwide live in low and middle-income countries (LMIC) where incidence and mortality rates of many medical conditions, such as cancers and cardiac diseases, are disproportionately high and adverse. Lack of access to imaging equipment, such as high resolution optical endoscopes, and well-trained medical technologists are among the major factors responsible for the delayed diagnosis, high morbidity and death rates in LMIC. Therefore, there is a need of affordable and easy-to-use high resolution endoscopes that can improve the diagnostic accuracy and treatment efficacy in low resource settings.

On the other hand, the cost of wireless technology has decreased significantly and the number of smartphones has increased tremendously throughout the world over the past decade, thereby making smartphone a very affordable, yet powerful device. The International Telecommunication Union estimated that there are 7 billion mobile phones subscribers globally (equivalent to 95.5% of the world population) in 2014 and more than 77% (5.4 billions) of these mobile phones are used in the LMIC. In addition to a high resolution camera, smartphones also offer enormous computation power, high-speed wireless Internet access, global positioning systems (GPS), gyros, and accelerometers etc., on a very compact platform. Smartphone-based diagnosis could potentially reduce health care costs and provide access to advanced laboratories and experienced physicians at remote locations. Smartphones in healthcare could revolutionize the field of telemedicine and point-of-care devices for diagnostics.

Previous efforts in mobile phone imaging have mostly focused on converting phone cameras to a low-cost, hand-held microscope or spectrometer. While phone-based optical microscopy and spectroscopy are actively studied for global health, however, no mobile phone or smartphone based endoscopes have been realized. The general method includes systems that employ a mobile phone or smartphone and associated software for performing optical imaging through an endoscope or microendoscope, as well as processing and transmission of endoscopic images.

In light of the increasing global endoscopy market, there is a need in the art to provide for an affordable and easy-to-use endoscopic device that can be used to improve such imaging capabilities in resource-poor settings.

SUMMARY OF THE INVENTION

In a first embodiment, the present invention provides a smartphone endoscope system comprising a smartphone including a first imaging sensor and a second imaging sensor, and an imaging optics attachment. The imaging optics attachment includes a first imaging apparatus and a second imaging apparatus. The first imaging apparatus includes a first light source producing excitation light, a beam splitter receiving the excitation light from the first light source and further reflecting the excitation light onto an objective lens, the objective lens further focusing the excitation light onto a fiber optic imaging bundle having a proximal end and a distal end. The fiber optic imaging bundle is configured to (1) deliver the excitation light to a target, (2) collect a fluorescence emission or a reflectance emission or both from the target, and (3) transmit the fluorescence emission or reflectance emission, or both, to the first imaging sensor. The second imaging apparatus includes a second light source providing broadband light, a DRS source fiber configured to receive broadband light and deliver broadband light to the target, a DRS detection fiber, a collimator, a slit, and a transmission grating. The DRS detection fiber is configured to collect a diffuse reflectance emission from the target and transmit the diffuse reflectance emission through a collimator, a slit, and transmission grating to the second imaging sensor.

In a second embodiment, the present invention provides a smartphone endoscope system as in the first embodiment, wherein the first light source is selected from an LED or a laser diode (LD).

In a third embodiment, the present invention provides a smartphone endoscope as in either the first or second embodiment, further comprising an optical filter receptacle positioned such that the reflectance and fluorescence emissions are transmitted to an optical filter before reaching the first imaging sensor, the optical filter removing the reflectance emission, wherein the optical filter is selectively employed.

In a fourth embodiment, the present invention provides a smartphone endoscope as in any of the first through third embodiments, further comprising an optical filter to block reflectance emission.

In a fifth embodiment, the present invention provides a smartphone endoscope system as in any of the first through fourth embodiments, wherein the optical filter is a long-pass filter.

In a sixth embodiment, the present invention provides a smartphone endoscope system as in any of the first through fifth embodiments, further comprising an eyepiece.

In a seventh embodiment, the present invention provides a smartphone endoscope system as in any of the first through sixth embodiments, wherein the eyepiece can be selected from a single lens or multiple lenses to focus light onto the first imaging sensor.

In an eighth embodiment, the present invention provides a smartphone endoscope system as in any of the first through seventh embodiments, wherein the imaging optics attachment includes a housing member, wherein the first light source, the beam splitter, the objective lens, the optical filter, the optical filter receptacle, the eyepiece, the second light source, the collimator, the slit, and the transmission grating are located within the housing.

In a ninth embodiment, the present invention provides a smartphone endoscope system as in any of the first through eighth embodiments, wherein the fiber optic imaging bundle, the DRS source fiber, and the DRS detection fiber extend outwardly from the housing member at different locations, and are further joined within a sleeve at a junction.

In a tenth embodiment, the present invention provides a smartphone endoscope system as in any of the first through ninth embodiments, wherein the fiber optic imaging bundle is connected by a first connector to the imaging optics attachment at a first location, and the DRS source fiber is connected by a second connector to the imaging optics attachment at a second location.

In an eleventh embodiment, the present invention provides a smartphone endoscope system as in any of the first through tenth embodiments, wherein the DRS detection fiber extends outwardly from the junction and is connected to the imaging optics attachment by a third connector at a third location, to communicate with the collimator, the slit, and the transmission grating.

In a twelfth embodiment, the present invention provides a smartphone endoscope system as in any of the first through eleventh embodiments, wherein the collimator transmits diffuse reflectance emissions from the DRS detection fiber through the slit.

In a thirteenth embodiment, the present invention provides a multimodal endoscope comprising a fiber optic imaging bundle, a DRS source fiber, and a DRS detection fiber joined in an elongate sleeve.

In a fourteenth embodiment, the present invention provides a multimodal endoscope as in the thirteenth embodiment, wherein the fiber optic imaging bundle forms an axially extending core structure and the DRS source fiber and the DRS detection fiber are located radially outward of the core structure.

In a fifteenth embodiment, the present invention provides a smartphone endoscope system, comprising a smartphone including a first imaging sensor and a second imaging sensor and an imaging optics attachment, comprising a first imaging apparatus and a second imaging apparatus. The first imaging apparatus includes a first light source producing excitation light, a beam splitter receiving excitation light from the first light source and further reflecting excitation light onto an objective lens, the objective lens further focusing excitation light onto a fiber optic imaging bundle having a proximal end and a distal end. The fiber optic imaging bundle delivering excitation light to a target and the target emitting a fluorescence emission and a reflectance emission both collected by the fiber optic imaging bundle and transmitted to the first imaging sensor. The second imaging apparatus includes a second light source providing broadband light, a DRS source fiber, the broadband light being launched into the DRS source fiber, which delivers broadband light to the target, the target producing a diffuse reflectance emission, a DRS detection fiber, a collimator, a slit, and a transmission grating, the DRS detection fiber transmitting the diffuse reflectance emission through a collimator, a slit, and a transmission grating, the transmission grating diffracting the diffuse reflectance emission and thus creating diffracted light, the diffracted light transmitted to the second imaging sensor, wherein the fiber optic imaging bundle, the DRS source fiber, and the DRS detection fiber are joined to provide an elongate multimodal endoscope.

In a sixteenth embodiment, the present invention provides a smartphone endoscope system comprising a smartphone including an imaging sensor and an imaging optics attachment. The imaging optics attachment includes an imaging apparatus including a light source producing excitation light, a beam splitter receiving the excitation light from the first light source and further reflecting the excitation light onto an objective lens, the objective lens further focusing the excitation light onto a fiber optic imaging bundle having a proximal end and a distal end, the fiber optic imaging bundle being configured to (1) deliver the excitation light to a target, (2) collect a fluorescence emission or a reflectance emission or both from the target, and (3) transmit the fluorescence emission or reflectance emission or both to the first imaging sensor.

In a seventeenth embodiment, the present invention provides a smartphone endoscope system comprising a smartphone including an imaging sensor and an imaging optics attachment. The imaging optics attachment includes an imaging apparatus including a light source providing broadband light, a DRS source fiber configured to receive the broadband light and deliver the broadband light to the target, a DRS detection fiber, a collimator, a slit, and a transmission grating, the DRS detection fiber configured to collect a diffuse reflectance emission from the target and transmit the diffuse reflectance emission through the collimator, the slit, and transmission grating to the imaging sensor.

DETAILED DESCRIPTION OF ILLUSTRATIVE EMBODIMENTS

The current invention describes a smartphone endoscope system using a smartphone for narrow-band imaging, fluorescence imaging, and diffuse reflectance spectroscopy (DRS). Immediate clinical applications of the device taught herein include, but are not limited to, early detection of cardiac diseases and cancers and pre-cancers of the gastrointestinal tract, cervix, colon, ovary, kidney, and prostate, etc.

Figure 1:
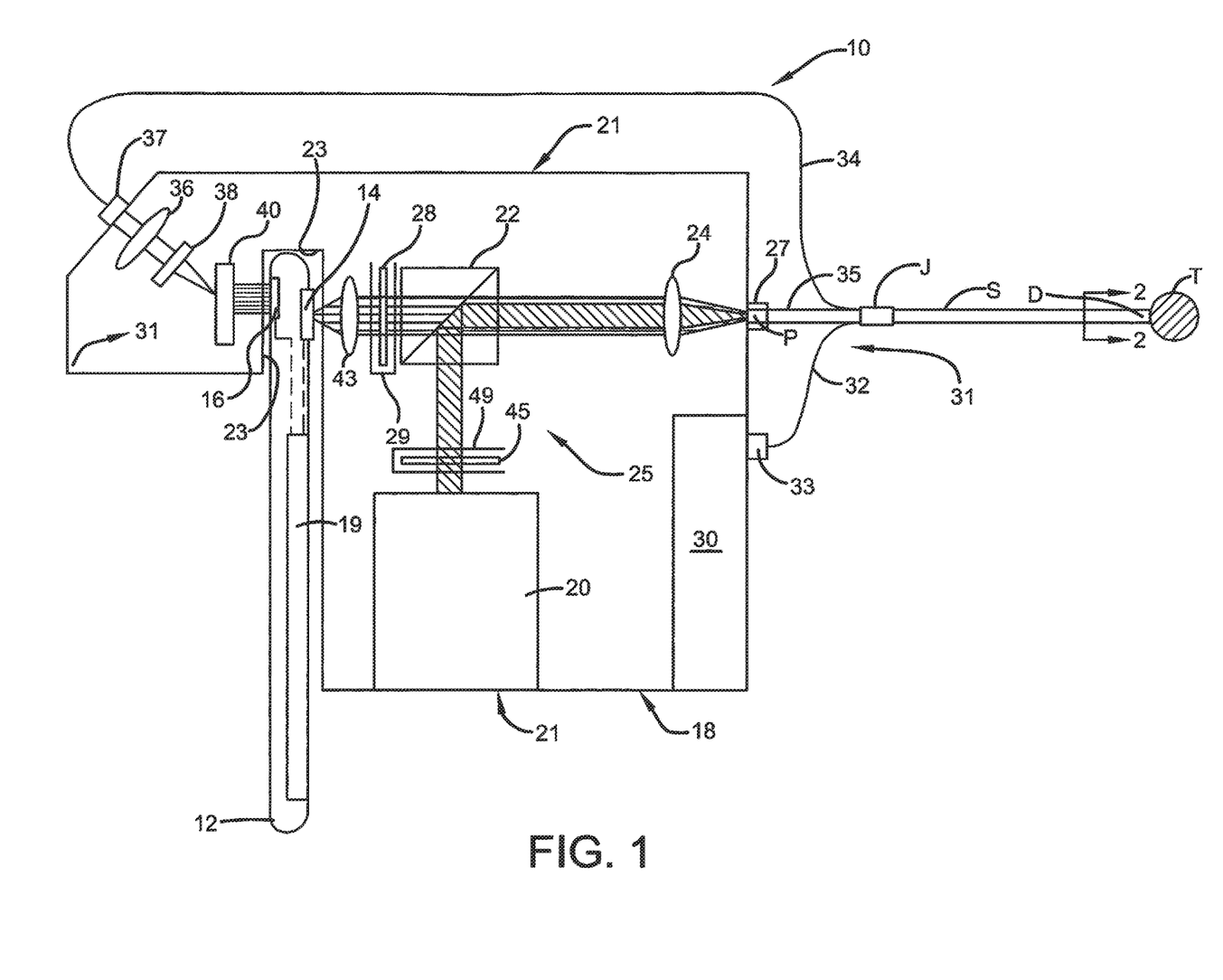
FIG. 1 is a schematic view of an embodiment of a smartphone endoscope system according to this invention.

With reference to FIG. 1, the present invention provides a smartphone endoscope system 10. The smartphone endoscope system 10 comprises a smartphone 12 and an imaging optics attachment 18. The smartphone 12 includes a first imaging sensor 14 and a second imaging sensor 16.

The smartphone 12 includes a microprocessor 19 with which the first imaging sensor 14 and second imaging sensor 16 communicate. The microprocessor 19 together with appropriate software, hardware, firmware, and the like, processes the light received by these imaging sensors and produces an image through known methods. The image may be produced on the phone screen (not shown) and/or transmitted to a remote computer for display and analysis through WiFi, 3G/4G networks, or can be hardwired such as through a USB cable, or the like, to produce an image on a screen or print a hard copy thereof, again as generally known. In some embodiments, the first imaging sensor 14 and the second imaging sensor 16 may be selected from CMOS sensor or CCD sensor.

The smartphone 12 is operatively connected to the imaging optics attachment 18. In some embodiments, the imaging optics attachment 18 includes a housing 21 attached at an imaging optics interface 23, schematically represented in FIG. 1 as a cavity appropriately sized to receive at least a part of the smartphone 12. A snap fit or other appropriate connection can be employed to associate the smartphone 12 with the imaging optics attachment 18 such that the imaging sensors receive the light necessary to create the desired images, as will be covered more fully below.

In some embodiments, the imaging optics attachment 18 is rigidly connected to the smartphone 12. In other embodiments, the smartphone 12 receives the imaging optics attachment 18 simply to appropriately align incoming light with the first imaging sensor 14 and second imaging sensor 16 as the case may be.

Figure 2:
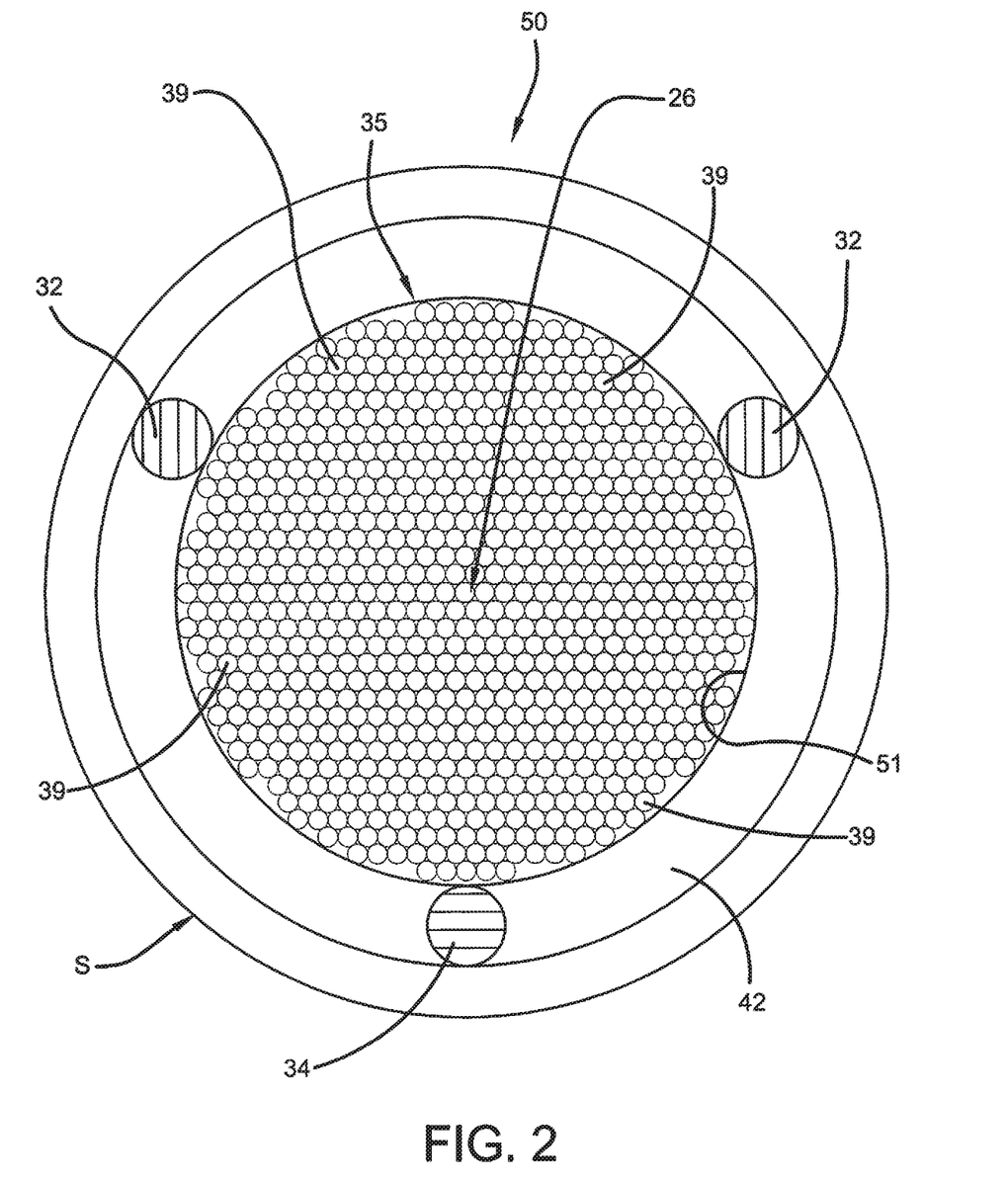
FIG. 2 is cross-section view of an embodiment of an elongate multimodal endoscope taken along the line 2-2 in FIGS. 1.

The imaging optics attachment 18 includes a first imaging apparatus 25. The first imaging apparatus 25 includes a first light source 20, a beam splitter 22, an objective lens 24, and a fiber optic imaging bundle 26 (FIG. 2). In some embodiments, the first light source 20, beam splitter 22, objective lens 24, and optical filter 28 are located within the housing 21. In such embodiments, the fiber optic imaging bundle 26 is connected to the housing 21 at a connector 27.

The first light source 20 produces excitation light to provide an excitation wavelength which causes a fluorescence emission by a target. In some embodiments, the light source 20 is selected to provide a suitable excitation wavelength to produce a fluorescence emission within a specific target. In some embodiments, the target may include any biological tissue. The excitation light wavelength necessary to produce a fluorescence emission in the target will be known for various types of targets, and the wavelength of the fluorescence emission will also be known, and appropriate light sources will be chosen to produce an appropriate excitation light depending upon the target to be analyzed.

In some embodiments, the light source 20 is selected from a light emitting diode (LED) or a laser diode (LD) to deliver excitation light to the target. In such embodiments, the light emitted from the LED or LD illuminates the tissue by utilizing the first imaging optics apparatus 25 located within the imaging optics attachment 18, and the fiber optic imaging bundle 26. In some embodiments, an optional bandpass filter 45 may be positioned between the light source 20 and the beam splitter 22 depending upon the breadth of the light spectrum provided by the light source 20 and the desired spectrum to deliver to the target through the beam splitter 22. In such embodiments, the optical bandpass filter 45 is positioned within an optical filter receptacle 49 which allows for optional installation of any of a plurality of different optical filters 45.

The beam splitter 22 receives light from the first light source 20 and reflects the excitation light onto an objective lens 24. The objective lens 24 focuses the excitation light onto the fiber optic imaging bundle 26. The fiber optic imaging bundle 26 transmits the excitation light to a target T for producing a fluorescence emission and a reflectance emission. As known in the art, the fiber optic imaging bundle 26 includes a plurality of optical fibers 39, (see FIG. 2 as an example). The fluorescence emission and reflectance emission are collected at the distal end D of the fiber optics imaging bundle 26 and ultimately transmitted to the first imaging sensor 14 of the smartphone 12 to be analyze by the aforementioned processor 19 to generate an image or other data related to the emissions of the target.

In some embodiments, the fiber optic imaging bundle 26 delivers both fluorescence emissions and reflectance emissions to the first imaging sensor 14. The fluorescence emissions and reflectance emissions are both transmitted to the first imaging sensor 14 by being transmitted back toward the proximal end P from the distal end D of the fiber optic imaging bundle 26, thereafter passing through the objective lens 24, which collimates the fluorescence and reflectance emissions and focuses them onto the beam splitter 22.

The beam splitter 22 receives fluorescence emission and diffuse reflectance emission from the target and allows both emissions to reach the first imaging sensor 14. The excitation light traveling to the target is reflected, and the fluorescence emission and diffuse reflectance emission from the target pass through the beam splitter 22 and are transmitted toward the imaging sensor 14.

The emissions pass through the beam splitter 22 to then reach an eyepiece 43 that focuses the emissions onto the first image sensor 14. The eyepiece 43 can be selected from a single lens or multiple lenses to focus the fluorescence emissions and reflectance emissions onto the first imaging sensor 14. In such embodiments, both fluorescence emissions and reflectance emissions are received by the first imaging sensor 14 to generate an image.

In other embodiments, the fiber optic imaging bundle 26 delivers only a fluorescence emission to the first imaging sensor 14. In such embodiments, the first imaging apparatus 25 includes an optical filter 28 in the light path between the beam splitter 22 and the imaging sensor 14. The optical filter 28 filters the emissions received back from the imaging bundle 26 to allow only a desired range of wavelengths to reach the imaging sensor 14. In some embodiments, the optical filter 28 is chosen to filter out the reflectance emission and thus only allow the fluorescence emission to reach the imaging sensor 14. In some embodiments, the optical filter 28 is a longpass filter. In other embodiments, the optical filter 28 may be selected from the group consisting of a longpass filter and a bandpass filter.

In some embodiments, the optical filter 28 is removably received in an optical filter receptacle 29. The optical filter receptacle 29 is located between the beam splitter 22 and the imaging sensor 14. The optical filter receptacle 29 allows for optional installation of any of a plurality of different optical filters 28. The optical filter 28 is selected to allow the transmission of the fluorescence emissions to pass through the optical filter 28, but rejects the wavelengths in the reflectance emissions. The optical filter receptacle 29 allows for the selection of an optical filter 28 to obtain the appropriate filter for filtering out the reflectance emissions received from the fiber optics imaging bundle 26. In some embodiments, the optical filter 28 is a longpass filter. In other embodiments, the optical filter 28 may be selected from the group consisting of a longpass filter and a bandpass filter.

In some embodiments, the optical filter 28 is permanently mounted within the optical filter receptacle 29.

With reference to FIGS. 1-2, the imaging optics attachment 18 further comprises a second imaging apparatus 31. The second imaging apparatus 31 includes a second light source 30, a DRS source fiber 32, a DRS detection fiber 34, a collimator 36, a slit 38, and a transmission grating 40. In some embodiments, the second light source 30, collimator 36, slit 38, and transmission grating 40 are located within the housing 21. In some embodiments, the second light source 30, collimator 36, slit 38, and transmission grating 40 are located within the housing 21, wherein the DRS source fiber 32 and DRS detection fiber 34 are connected to the housing 21.

The second imaging apparatus 31 utilizes DRS, wherein a beam of broadband light is emitted from a second light source 30 and is launched into a target or tissue for quantification. DRS is sensitive to the absorption and scattering properties of epithelial tissue and is suitable for the early diagnosis of cancers, such as those found in the oral cavity, cervix, colon, and Barrett's esophagus. The absorption (μa) and reduced scattering coefficients (μs') of epithelial tissues reflect their underlying physiological and morphological properties.

For example, dominant absorbers in the visible wavelength range in cervical tissues include oxy-hemoglobin and deoxy-hemoglobin, arising from blood vessels in the stroma. Light scattering is primarily caused by cell nuclei and organelles in the epithelium and stroma, as well as collagen fibers and cross-links in stroma. Neoplastic epithelial tissue exhibits significant changes in their physiological and morphological characteristics that can be quantified optically given that the stromal layer absorption is expected to increase with angiogenesis, resulting in decreased stromal scattering with neoplastic progression that coincides with the degradation of extracellular collagen networks. In contrast, epithelial scattering increases due to increased nuclear size and DNA content, as well as hyperchromasia.

In the visible band, DRS has a penetration depth that can be tuned to be comparable to the thickness of the epithelial layer or deeper to probe both the epithelial and stromal layers, enabling DRS to be used as a cost-effective, fast and sensitive tool for early diagnosis of precancerous changes, for example, as in the cervix.

The second light source 30 provides broadband light to the DRS source fiber 32. In some embodiments, the second light source 30 produces broadband light provided by light sources selected from thermal lamps, white LEDs, LEDs, and LDs. In some embodiments, the DRS source fiber 32 is a multimode optical fiber. The DRS source fiber 32 is connected to the housing 21 to be part of the imaging optics attachment 18 by a second connector 33. The broadband light from the second light source 30 is launched into the DRS source fiber 32, which extends to contact the target T and delivers light to target T. The target T will produce a diffuse reflectance emission that is collected by the DRS detection fiber 34 (also in contact with the target T) and ultimately delivered to the second imaging sensor 16. In some embodiments, the DRS detection fiber 34 communicates with the housing at a separate location at a third connector 37.

The DRS detection fiber 34 of the present invention collects diffuse reflectance that is reflected from a target or tissue. Once the diffuse reflectance is collected by the DRS detection fiber 34, the diffuse reflectance passes through a collimator 36, and is further relayed to a slit 38 positioned in front of a transmission grating 40. The broadband reflectance is diffracted by the transmission grating 40 and transmitted to and detected by the second imaging sensor 16 of the smartphone 12 which generates a diffuse reflectance spectrum.

In some embodiments, the collected diffuse reflectance spectrum is analyzed by an algorithm. The reflectance spectrum is analyzed through known techniques using a model of photon propagation in tissue (e.g., diffusion equation, Monte Carlo simulation or empirical model) to extract the absorption and reduced scattering coefficients. From the absorption spectrum, the concentrations of the absorbers (such as oxy-hemoglobin, deoxy-hemoglobin, beta-carotene and melanin, etc.) can be computed using the Beer-Lambert law (also known as Beer's law). The scattering reflects the tissue morphological information, such as nuclear size and density. Both tissue compositions and morphological information have been identified as useful biomarkers for cancer diagnostics.

It will be appreciated that the imaging bundle 26 disclosed herein typically will be provided inside of a sleeve 51, the sleeve 51 and imaging bundle 26 (optical fibers 39) forming a fiber optic endoscope 35. Although the fiber optics imaging bundle 26 can be provided separately from the DRS source fiber 32, and DRS detection fiber 34, in some embodiments, all are combined into a novel multimodal endoscope 50, as shown in cross-section in FIG. 2. The fiber optics imaging bundle 26 (or fiber optics endoscope 35 when the sleeve 51 is employed), the DRS source fiber 32, and the DRS detection fiber 34 are connected to the imaging optics attachment 18 at three separate locations at connectors 27, 33, and 37, respectively, and are all joined at the junction, J. At the junction J, the fiber optics imaging bundle 26, the DRS source fiber 32 and the DRS detection fiber 34 are collectively retained within a sleeve, S, forming a multimodal endoscope 50.

As shown in FIG. 2, the multimodal endoscope 50 includes the fiber optic endoscope 35, the DRS source fiber 32, and the DRS detection fiber 34. The fiber optic endoscope 35 is further encased in sleeve S, and an annular space 42 is defined between the exterior of the sleeve 51 and the interior of sleeve S. In some embodiments, the DRS source fiber 32 and the DRS detection fiber 34 are retained in the annular space 42. In some embodiments, the fiber optic imaging bundle 26 is coaxial with the sleeve S, forming a core structure thereof, wherein the DRS source fiber 32 and the DRS detection fiber 34 are located radially outward of this core structure. In some embodiments, the DRS source fiber 32 and the DRS detection fiber 34 are glued to either the exterior of sleeve 51 of the interior of sleeve S or both. This gluing may be along the entire length of the multimodal endoscope 50 or at only a portion thereof. In some embodiments, the DRS source fiber 32 and the DRS detection fiber 34 are glued to the distal end of the fiber optic imaging bundle 26, i.e., at exterior of sleeve 51. In other embodiments, the annular space 42 is packed with material to hold the DRS source fiber 32 and the DRS detection fiber 34 in place.

Figure 3:
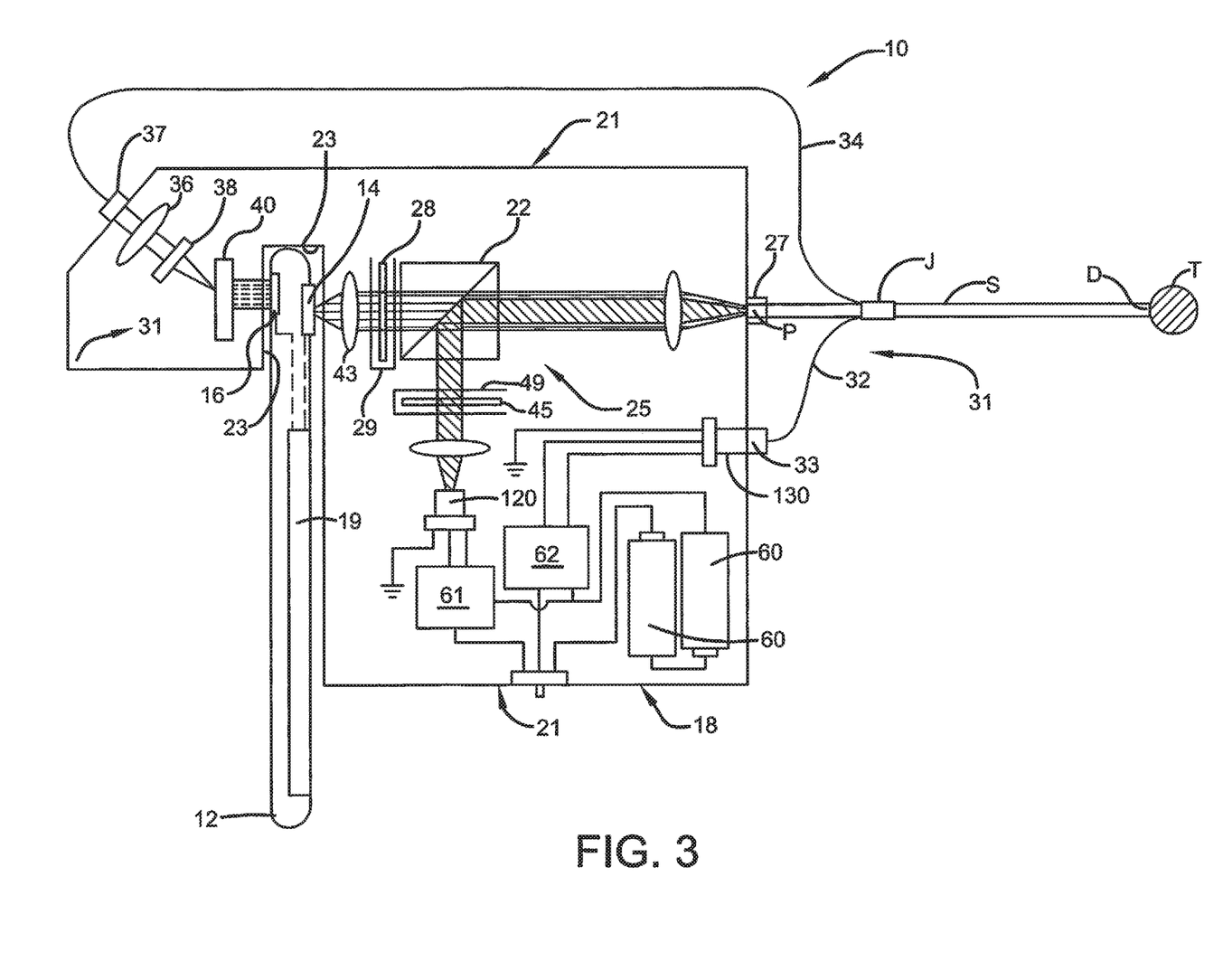
FIG. 3 is a schematic view of another embodiment of a smartphone endoscope system in accordance with the present invention.

As shown in FIG. 3, like parts to those of the embodiments of FIG. 1 receive like numerals, and the disclosure above can be referred to for their disclosure. The purpose of FIG. 3 is to help disclose particular structure for light source 120 and broadband light source 130. The first and second light sources 120 are driven by a power source. In some embodiments, the power source is a battery or batteries 60 or DC power supply or other mains power supply.

As compared to FIG. 1, the embodiment of FIG. 3 provides a first light source 120 in the form of an LED, laser diode (LD), a thermal lamp or broadband source or the like. In some embodiments the first light source 120 is a blue LED to provide for narrowband imaging and fluorescence excitation of certain fluorophores. In some embodiments, other colored LEDs may be required for other fluorophores. Notably, the optical filter 45 can optional be employed to limit the light to desired spectrums if the light source itself provides too broad a spectrum. For example a broadband LED might be used with an appropriate optical filter 45.

In some embodiments, the light source 120 includes a driver 61 to maintain a stable current. A stable current supply is required for providing power to the light source 120, as the performance of light source 120 depends upon the stability of the current supplied to it. The light source driver 61 supplies a linear current to the light source 120 providing temperature stability, i.e. the current remains stable over a temperature range thereby maintaining the brightness of the light source 120, and further maintaining a stable current thereby producing a constant output. In some embodiments, the light source driver 61 is selected from an LED driver or LD driver. It should be appreciated that when the light source 120 is a LD, the light source driver 61 is selected from an LD driver.

In some embodiments, the light source 120 is an LED light source and includes a light source driver 61 to maintain a stable current. A stable current supply is required for providing power to the LED light source, as the performance of the LED light source depends upon the stability of the current supplied to it. The light source driver supplies a linear current to the LED light source providing temperature stability, i.e. the current remains stable over a temperature range thereby maintaining the brightness of the LED light source over that temperature range. The light source driver further maintains a stable current supplied to the LED light source, thereby producing a constant output.

As compared to FIG. 1, the embodiment of FIG. 3 provides a broadband light source 130 in the form of a thermal lamp, a white LED, a LED, and a LD, chosen so long as they provide a broad spectrum useful for DRS. In some embodiments, a driver 62 is used to maintain a stable current. The light source driver 62 supplies a current to the broadband light source 130 providing temperature stability, i.e. the current remains stable over a temperature range thereby maintaining the brightness of the light source 130, and further maintaining a stable current thereby producing a constant output. In some embodiments, the light source driver 62 is selected from a LED driver or a constant current source. In some embodiments, the broadband light source is a broadband LED driven by an LED driver.

Notably, each of the imaging apparatuses 25 and 31 could be practiced separately simply by avoiding the inclusion of one or the other in an appropriate housing 21. Thus, having disclosed both apparatuses 25 and 31, it will readily be appreciated that a smartphone with only one such apparatus is also disclosed and enabled.

In light of the foregoing, it should be appreciated that the present invention significantly advances the art by providing a high resolution smartphone endoscope system that is structurally and functionally improved in a number of ways. An advancement is also provided by the multimodal endoscope structure described herein and the combination of the same with the smartphone endoscope system. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A smartphone endoscope system comprising:
a smartphone including a first imaging sensor and a second imaging sensor; and
an imaging optics attachment comprising,
(a) a first imaging apparatus including:
a first light source producing excitation light,
a beam splitter receiving said excitation light from said first light source and further reflecting said excitation light onto
an objective lens, said objective lens further focusing said excitation light onto
a fiber optic imaging bundle having a proximal end and a distal end, said fiber optic imaging bundle being configured to (1) deliver said excitation light to a target, (2) collect a fluorescence emission or a reflectance emission or both from the target, and (3) transmit said fluorescence emission or reflectance emission or both to said first imaging sensor; and
(b) a second imaging apparatus including:
a second light source providing broadband light,
a DRS source fiber configured to receive said broadband light and deliver said broadband light to the target,
a DRS detection fiber,
a collimator,
a slit, and
a transmission grating, said DRS detection fiber configured to collect a diffuse reflectance emission from the target and transmit said diffuse reflectance emission through said collimator, said slit, and transmission grating to said second imaging sensor.

2. The smartphone endoscope system as in claim 1, wherein said first light source is selected from an LED or a laser diode (LD).

3. The smartphone endoscope system as in claim 1, further comprising an optical filter receptacle positioned such that the reflectance and fluorescence emissions are transmitted to an optical filter before reaching the first imaging sensor, the optical filter removing the reflectance emission, wherein said optical filter is selectively employed.

4. The smartphone endoscope system as in claim 1, further comprising an optical filter to block reflectance emission.

5. The smartphone endoscope system as in claim 4, wherein said optical filter is a longpass filter.

6. The smartphone endoscope system as in claim 1, further comprising an eyepiece for focusing said fluorescence emissions onto said first imaging sensor.

7. The smartphone endoscope system as in claim 6, wherein said eyepiece can be selected from a single lens or multiple lenses to focus light onto said first imaging sensor.

8. The smartphone endoscope system as in claim 1, wherein said imaging optics attachment includes a housing member, wherein said first light source, said beam splitter, said objective lens, an optical filter, an optical filter receptacle, an eyepiece, said second light source, said collimator, said slit, and said transmission grating are located within said housing.

9. The smartphone endoscope system as in claim 1, wherein said fiber optic imaging bundle, said DRS source fiber, and said DRS detection fiber extend outwardly from said housing member at different locations, and are further joined within a sleeve at a junction.

10. The smartphone endoscope system as in claim 9, wherein said fiber optic imaging bundle is connected by a first connector to said imaging optics attachment at a first location, and said DRS source fiber is connected by a second connector to said imaging optics attachment at a second location.

11. The smartphone endoscope system as in claim 10, wherein said DRS detection fiber extends outwardly from said junction and is connected to said imaging optics attachment by a third connector at a third location, to communicate with said collimator, said slit, and said transmission grating.

12. The smartphone endoscope system as in claim 1, wherein said collimator transmits diffuse reflectance emissions from said DRS detection fiber through said slit.

13. A smartphone endoscope system comprising:
 a smartphone including a first imaging sensor and a second imaging sensor; and
 an imaging optics attachment, comprising,
  (a) a first imaging apparatus including:
   a first light source producing excitation light,
   a beam splitter receiving said excitation light from said first light source and further reflecting said excitation light onto
   an objective lens, said objective lens further focusing said excitation light onto
   a fiber optic imaging bundle having a proximal end and a distal end, said fiber optic imaging bundle delivering said excitation light to a target and the target emitting a fluorescence emission and a reflectance emission both collected by said fiber optic imaging bundle and transmitted to said first imaging sensor; and
  (b) a second imaging apparatus including:
   a second light source providing broadband light,
   a DRS source fiber, said broadband light being launched into said DRS source fiber, which delivers broadband light to the target, the target producing a diffuse reflectance emission,
   a DRS detection fiber,
   a collimator,
   a slit, and
   a transmission grating, said DRS detection fiber transmitting said diffuse reflectance emission through said collimator, said slit, and transmission grating, said transmission grating diffracting said diffuse reflectance emission and thus creating diffracted light, said diffracted light transmitted to said second imaging sensor, wherein said fiber optic imaging bundle, said DRS source fiber, and said DRS detection fiber are joined to provide an elongate flexible fiber optic endoscope cable.

* * * * *